US00PP25604P3

(12) United States Plant Patent
Egger

(10) Patent No.: US PP25,604 P3
(45) Date of Patent: May 26, 2015

(54) ***HEUCHERA* PLANT NAMED 'LIME RUFFLES'**

(50) Latin Name: ***Heuchera* hybrid**
Varietal Denomination: Lime Ruffles

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 175 days.

(21) Appl. No.: 13/986,955

(22) Filed: Jun. 18, 2013

(65) Prior Publication Data
US 2014/0373238 P1 Dec. 18, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant substantially as shown and described, characterized by large, ruffled, lime green leaves with a white veil, a medium plant size, showy white flowers in late summer, and good vigor.

1 Drawing Sheet

Botanical denomination: *Heuchera* hybrid.
Variety designation: 'Lime Ruffles'.

BACKGROUND OF THE INVENTION

The present invention relates to a new and distinct cultivar of *Heuchera* and given the cultivar name of 'Lime Ruffles'. *Heuchera* is in the family Saxifragaceae. *Heuchera* 'Lime Ruffles' originated from a planned cross between *Heuchera* K587-2, a proprietary unreleased plant, as the seed parent, and *Heuchera* 'Marmalade', (U.S. Plant Pat. No. 15,945) as the pollen parent. Compared to the seed parent, *Heuchera* K587-2, the new cultivar has lime rather than purple to blue green foliage and white rather than pink flowers. Compared to the pollen parent, *Heuchera* 'Marmalade', the new cultivar has leaves that are larger and lime with a veil rather than amber, and has white flowers rather than green white.

Compared to *Heuchera* 'Lime Marmalade' (U.S. Plant Pat. No. 21,861), the new cultivar has a rounder habit, larger leaves that are veiled rather than unveiled and larger flowers that are white rather than green white.

Compared to *Heuchera* 'Lime Rickey' (U.S. Plant Pat. No. 16,210), the new cultivar has larger leaves which are veiled, a larger, rounder habit and larger flowers.

This new *Heuchera* is distinguished by:

1. large, veiled, ruffled, lime green leaves,
2. medium plant size,
3. showy white flowers in late summer, and
4. good vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an 8 month-old *Heuchera* 'Lime Ruffles' grown in shade in a container in August in Canby, Oreg.

FIG. 2 shows a group of 9 month-old *Heuchera* 'Lime Ruffles' in flower growing in shade in the trial bed in September in Canby, Oreg.

DETAILED PLANT DESCRIPTION

The following is a detailed description of the new *Heuchera* cultivar based on observations of 9 month-old specimens grown in the ground in the trial bed in shade in October in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* $5^{th}$ edition, 2007.

Plant:

*Form.*—Basal rosette, herbaceous perennial.
*Hardiness.*—USDA Zone 4 to 9.
*Size.*—17 cm tall from top of the foliage to the ground and 40 cm wide.
*Habit.*—Mound.
*Vigor.*—Excellent.
*Roots.*—Fibrous, freely branching, fine, and white in color; roots develop easily from stem cuttings.

Leaf:

*Type.*—Simple.
*Arrangement.*—Basal.
*Shape.*—Broadly ovate.
*Lobing/division.*—5 main lobes, with 2 to 3 shallow secondary lobes.

*Venation.*—Palmate, veins topside Yellow 4C, bottom side Yellow Green 145B.

*Margins.*—Crenate and undulate.

*Apex.*—Mucronulate.

*Base.*—Cordate, lobes overlapping at the base.

*Blade size.*—Grows to 11 cm long and 10 cm wide.

*Surface texture.*—Both sides glandular hairs.

*Petiole description.*—Grows to 14.5 cm long and 2.5 mm wide, glandular hairs, Yellow Green 145B.

*Leaf color.*—Spring and fall new growth topside Yellow Green 145A with a white veil of Yellow 4D, bottom side Yellow Green 147B; summer and winter topside Yellow Green 144A with the veil Greyed Green 193C, bottom side closest to Yellow Green 147C.

Inflorescence:

*Size.*—Grows to 7 cm wide and 34.5 cm long.

*Type.*—Thyrse.

*Number of flowers per thyrse.*—100 to 160 per thyrse.

*Number of thyrse.*—About 6 in spring bloom.

*Peduncle.*—Grows to 45 cm tall, 2.5 mm wide at base, Yellow Green 145C at base blending to Greyed Yellow 162B, glandular hairs, with 1 to 4 petiolate leaves (ovate, blades grow to 5 cm long and 5.5 cm wide, 5 lobed, margin biserrate, color the same as the leaves).

*Pedicel.*—1 mm to 4 mm long, with glandular hairs, Yellow Green 145D in shade and Greyed Red 181B in sun.

*Bloom period.*—September to October in Canby, Oreg.

Flower bud:

*Size.*—3.5 mm wide and 4 mm long.

*Description.*—Glandular puberulent, ovoid.

*Color.*—Top half White 155C, bottom half Yellow Green 154D.

Flower:

*Type.*—Perfect.

*Shape.*—Campanulate.

*Size.*—5 mm long and 4.5 mm wide.

*Petal description.*—5 in number, 3 mm long and 1 mm wide, reflexed, spatulate with a clawed base, tip acute, margin entire, glabrous on top and bottom sides, sometimes glandular puberulent, White NN155C on both sides.

*Calyx description.*—4 mm long and 4 mm wide, with 5 lobes, divided ½ way to the base, glandular hairs on outside, glabrous inside, tip obtuse, margin entire, both sides top half White 155C, bottom half Yellow Green 154D.

*Stamen description.*—5 in number, each 3.5 mm long, White NN155C, anthers Yellow Orange 21C, no pollen, male sterile.

*Pistil description.*—One central two beaked pistil, 4 mm long, ovary 1 mm long and Green Yellow 1D, style 3 mm long , White 155C.

*Fragrance.*—None.

*Lastingness.*—Each thyrse blooms for about 2 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Disease and pest tolerance: Pest and disease resistance are typical for this type of *Heuchera*. No known resistances.

I claim:

1. A new and distinct *Heuchera* plant as herein illustrated and described.

* * * * *

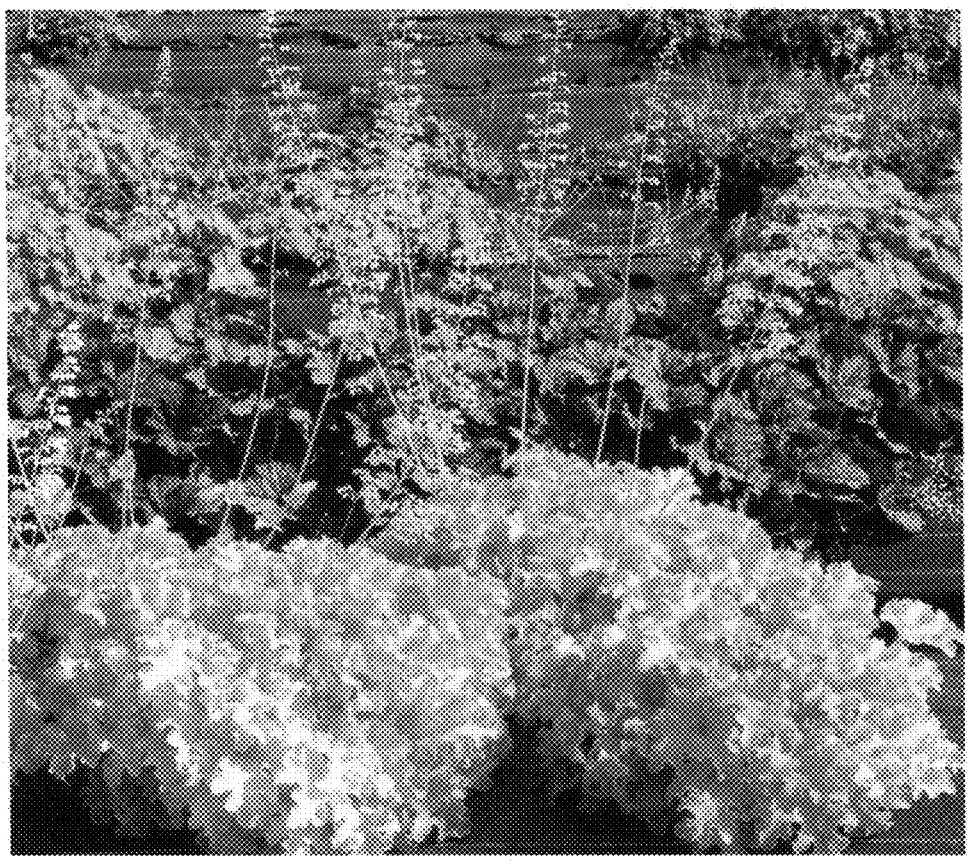

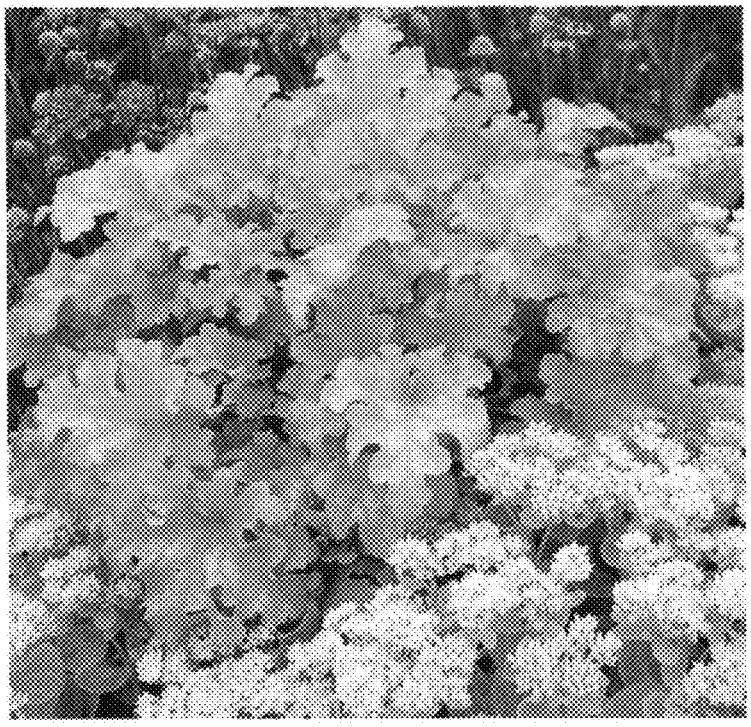
FIG. 1 to left,
FIG. 2 below